(12) United States Patent
Lacabanne

(10) Patent No.: US 7,132,089 B2
(45) Date of Patent: Nov. 7, 2006

(54) SET FOR STERILISING MEDICAL INSTRUMENTS OR APPLIANCES

(75) Inventor: Jean-Paul Lacabanne, Balma (FR)

(73) Assignee: Metrolog, Services Metrologiques, Toulouse (FR)

( * ) Notice: Subject to any disclaimer, the term of this patent is extended or adjusted under 35 U.S.C. 154(b) by 646 days.

(21) Appl. No.: 10/258,239

(22) PCT Filed: Apr. 23, 2001

(86) PCT No.: PCT/FR01/01237

§ 371 (c)(1),
(2), (4) Date: Oct. 22, 2002

(87) PCT Pub. No.: WO01/80908

PCT Pub. Date: Nov. 1, 2001

(65) Prior Publication Data

US 2003/0091471 A1 May 15, 2003

(30) Foreign Application Priority Data

Apr. 25, 2000 (FR) .................................. 00 05229

(51) Int. Cl.
*A61L 2/24* (2006.01)
(52) U.S. Cl. .................... 422/292; 422/116; 206/363; 206/436
(58) Field of Classification Search ............... 422/296, 422/116; 236/48 A; 206/363, 439
See application file for complete search history.

(56) References Cited

U.S. PATENT DOCUMENTS

| | | | | |
|---|---|---|---|---|
| 4,748,003 A | * | 5/1988 | Riley | 422/112 |
| 4,948,566 A | * | 8/1990 | Gabele et al. | 422/107 |
| 5,019,345 A | * | 5/1991 | Lorenz | 422/26 |
| 5,097,865 A | * | 3/1992 | Riley | 137/529 |
| 5,176,884 A | * | 1/1993 | Taschner et al. | 422/292 |
| 5,277,876 A | * | 1/1994 | Wagner | 422/110 |
| 5,352,416 A | * | 10/1994 | Wagner | 422/108 |
| 5,368,821 A | * | 11/1994 | Schmoegner et al. | 422/116 |
| 6,010,670 A | * | 1/2000 | Berry, Jr. | 422/295 |

FOREIGN PATENT DOCUMENTS

| | | |
|---|---|---|
| DE | 36 32 674 | 4/1988 |
| EP | 0 630 820 | 12/1994 |

* cited by examiner

Primary Examiner—E. Leigh McKane
(74) Attorney, Agent, or Firm—Young & Thompson

(57) ABSTRACT

The invention relates to a serialization set, in particular for surgical instruments or appliances, consisting of a container and an electronic apparatus (17) for recording at least one serialization parameter. The container includes a valve (11) arranged opposite a wall (7) of said container capable of allowing a sterilizing agent to penetrate, said valve being stressed towards a closed position by elastic means (29) and comprising catching members (15) capable of extending through the wall (7) when a force is exerted on said valve (11) countering the action of the elastic means (29). The electronic apparatus (17), designed to be attached to the container wall (7), comprises means for locking (19, 21) the catching members (15) of the valve (11) and automatic disengaging means (25) for producing the release of these catching members, once the serialization parameters are fulfilled.

14 Claims, 5 Drawing Sheets

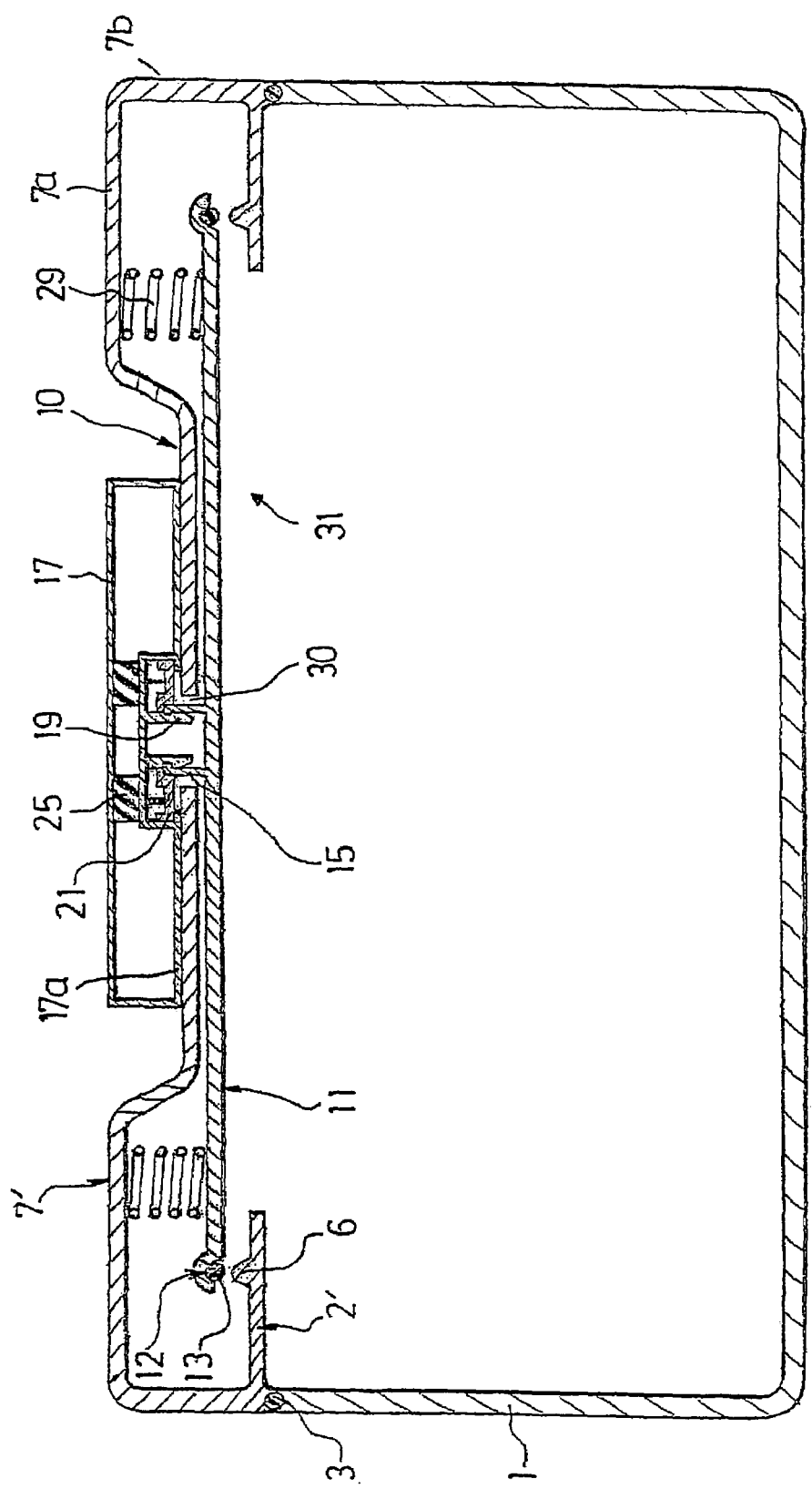

SET FOR STERILISING MEDICAL INSTRUMENTS OR APPLIANCES

BACKGROUND OF THE INVENTION

The invention relates to a serialization set, in particular for medical instruments or appliances.

In care centers, pharmaceutical laboratories or other establishments which have to ensure the serialization of appliances or instruments, use is made of metallic containers, the purpose of which is to contain in particular surgical instruments during the serialization phase, and then to preserve their sterile state.

To date, these containers are of two main types:
  containers with a filter: a specific paper filter permits the passage of the steam, but does not permit the passage of the germs which could contaminate the product,
  containers with valves: a system of valves permits the passage of the steam and its extraction and closes to ensure the sealing of the container.

In practice, however, these two types of containers are not entirely satisfactory. Paper filters can be damaged and therefore no longer ensure "tightness" against germs. Valves, for their part, do not always ensure proper sealing.

In order to overcome these disadvantages, the consequences of which can be very harmful to the health of the patients, two other solutions have been proposed up to now.

The first of these solutions described in the patent U.S. Pat. No. 4,948,566 consists in proposing a serialization unit having a central unit for checking the serialization parameters, a plurality of locking members distributed in the serialization chamber, which are designed to produce the opening and closure of the containers arranged in the latter.

Although this solution appears satisfactory from the point of view of the quality of the serialization, it nevertheless has the disadvantage of requiring very specific serialization units, and containers dedicated to these serialization units. Consequently, it necessitates renewal of the serialization units and the containers in their entirety, and it proves to be very costly.

The second solution described in the patent DE 3,632,674 consists in proposing a container having, incorporated in the lid of said container, electronic means for checking at least one serialization parameter, at least one energy storage device, a control unit controlled by the checking means and designed, on receiving a signal emitted by these checking means, to release the energy from the storage devices and bring about the closure of the lid.

Although such containers also appear satisfactory from the point of view of the quality of the serialization, they nevertheless have a major disadvantage. According to this solution, all the controlling and checking means are incorporated in the lid of each container during manufacture, and said containers are consequently very costly. Moreover, the technical realization of such containers proves to be very difficult.

Furthermore, in parallel with these solutions, and with the aim of ensuring a high-quality serialization and of being able to check it for complete traceability of the medical devices from decontamination to reuse, it is necessary to check that the serialization parameters have actually been achieved. To this end, until the recent past, the use of paper integrators and biochemical analyses performed this role. For some years, independent electronic pressure and temperature recorders have made it possible to check, by reading the data recorded in their internal memory, that the serialization parameters have been achieved and therefore to validate the cycle in question. This method is sometimes called "parametric release of the loads". Apparatuses of this type are produced, moreover, by the applicant under the registered trade names "STERILOG" and "MICROLOG".

SUMMARY OF THE INVENTION

The present invention aims to use this technology and proposes to provide a serialization set incorporating a container and an electronic recorder, on the one hand whose cost is substantially equivalent to that of the current containers and recorders, and on the other hand which guarantees that the serialization parameters have been met.

To this end, the invention is aimed at a serialization set, in particular for medical instruments or appliances, having a container comprising a receptacle and means for obturating said receptacle which are capable of obturating it in a sealed manner, and electronic means for recording at least one serialization parameter during the serialization phases.

According to the invention, this serialization set has the following features:
  the container comprises:
    a valve arranged inside the container opposite a wall, called a sterilisation wall, of said container, said wall being arranged to permit a sterilizing agent to penetrate into said container,
    a seat for supporting the valve, said seat being formed inside the container so that said valve ensures the obturation of the receptacle, in a closed position,
    sealing means capable of ensuring a seal between the valve and its supporting seat in the closed position of said valve,
    elastic means arranged between the sterilisation wall and the valve so as to stress said valve towards its position of closing the receptacle,
    and catching means made in one piece with the valve and arranged to extend outside the container through an orifice formed in the sterilisation wall, when a force is exerted on said valve countering the elastic means, designed to bring said valve towards a position of opening the receptacle.
  the electronic recording means comprise an independent electronic apparatus designed to be attached to the sterilisation wall of the container, said electronic apparatus:
  comprising locking means designed to cooperate with the catching members of the valve, so as to keep the latter in its open position,
  comprising means for automatically disengaging the locking means for producing the release of the catching members of the valve and allowing the movement of the latter towards its closed position under the action of the elastic means,
  being programmed to activate the disengaging means when every sterilisation parameter is met.

According to the invention, the control of the closure of the valve as a function of sterilisation parameters is obtained by virtue of the original catching and locking means with which said valve and the independent electronic recording apparatus are equipped.

This control is therefore obtained by the use of containers and electronic apparatuses of a cost substantially equivalent to that of the current containers and electronic apparatuses. Moreover, since the electronic apparatus, which constitutes the element of appreciably the highest cost, is separable from the container after sterilisation, the number of such electronic apparatuses required in an establishment is much lower than that of the containers, and at most equal to the capacity of the sterilisers.

In contrast to the device described in the patent DE-3,632,674, the invention has thus consisted in providing a very original solution which permits dissociation of the electronic apparatus automatically from the container after sterilisation, hence a cost of the containers comparable to that of the current conventional containers, and a number of electronic apparatuses required which is much lower than that of the containers, and comparable to that required at present.

Moreover, it should be emphasised that the sterilisation set according to the invention makes it possible to guarantee that the sterilisation parameters have been achieved before closing the sterilisation container in a reliable and controlled manner.

According to an advantageous embodiment of the invention:
the sterilisation wall consists of a lid, called an over-lid, of a shape designed to cap the receptacle and equipped with means for securing to said receptacle,
the seat for supporting the valve consists of a lid of a shape designed to cover the receptacle, and containing at least one orifice for the passage of a sterilising agent, which can be obturated by said valve in the closed position of the latter,
sealing means are arranged between the receptacle and the lid so as to ensure the sealing of the container in the closed position of the valve.

According to this embodiment, the container therefore has an over-lid which serves as a support for the electronic apparatus and which permits the compression of the elastic means during the movement of the valve towards its open position, and a lid which serves as a seat for the valve and ensures the sealing of the container in the closed position of said valve. According to this embodiment, two advantageous embodiment versions may, additionally, be envisaged:
According to the first version, the lid and the over-lid are made in one piece so as to form an assembly separable from the receptacle and incorporating the valve,
According to the second version, the lid and the over-lid consist of two distinct elements, the valve being arranged under the over-lid and connected to the latter by the elastic means.

Furthermore, in an advantageous manner, according to the invention, the lid contains a central orifice, the valve consisting of a plate equipped at the lower face with a guiding pin capable of sliding in said orifice. This guiding of the valve makes it possible to guarantee the perfect coincidence of the sealing means arranged between said valve and the lid.

Moreover, as regards these sealing means, the lid advantageously has a central portion containing a plurality of orifices for the passage of a sterilising agent, the valve consisting of a plate designed to cover said central portion, and said lid and valve having sealing means formed so as to be situated on the circumference of this central portion.

Furthermore, the over-lid advantageously has a central indented zone of dimensions designed to accommodate the electronic apparatus. Such an indentation makes it possible to stack the containers fitted with their electronic apparatus with a view in particular to storing them.

Moreover, in order to facilitate the penetration of the sterilising agent, the over-lid advantageously contains at least one orifice.

According to another advantageous embodiment, the catching means of the valve, and the elastic means stressing said valve towards its position of closing the receptacle, are designed so that said catching means do not project outside the sterilisation wall in the closed position of the valve. This arrangement makes it possible to protect these catching means from any risk of damage, once the electronic apparatus is separated from the container.

According to another advantageous embodiment of the invention:
the catching means of the valve and the locking means of the electronic apparatus have two rings of shapes designed to fit into each other, and equipped with members for relative blocking in terms of axial translation, one of said rings being composed of radially flexible fingers,
the locking means of the electronic apparatus have a locking member arranged so as to be pushed back by the catching members of the valve during the movement of the latter towards its open position, and stressed by elastic means capable of keeping it in a position of radially stopping the flexible fingers,
the automatic disengaging means are designed to bring about a movement of the locking member, countering the action of the elastic means, towards a position in which it releases the flexible fingers.

In this case, additionally, and in an advantageous manner, according to the invention:
the catching means of the valve consist of the ring composed of flexible fingers, said ring being of a shape designed to slide on the outside of the ring of the locking means of the electronic apparatus,
the locking member of the electronic apparatus consists of an annular part of a shape designed to enclose the flexible fingers.

Moreover, and in an advantageous manner, according to the invention:
the ring of the locking means of the electronic apparatus has an end section possessing a conical outer face forming a ramp for insertion inside the ring of the valve,
the members for blocking the rings in terms of translation consist of an annular boss and an annular groove of mating shapes, the blocking member formed on the flexible fingers being situated at the end of the latter,
the locking member is made from a magnetic material, the means for disengaging said locking member consisting of an electromagnet.

BRIEF DESCRIPTION OF THE DRAWINGS

Other features, objects and advantages of the invention will emerge from the detailed description which follows with reference to the attached drawings which show, by way of non-limiting examples, two preferred embodiments thereof.

In these drawings:
FIG. 5 is an axial section in the plane A showing an alternative embodiment of a sterilisation set according to the invention.

DESCRIPTION OF THE PREFERRED EMBODIMENTS

Figure 1:
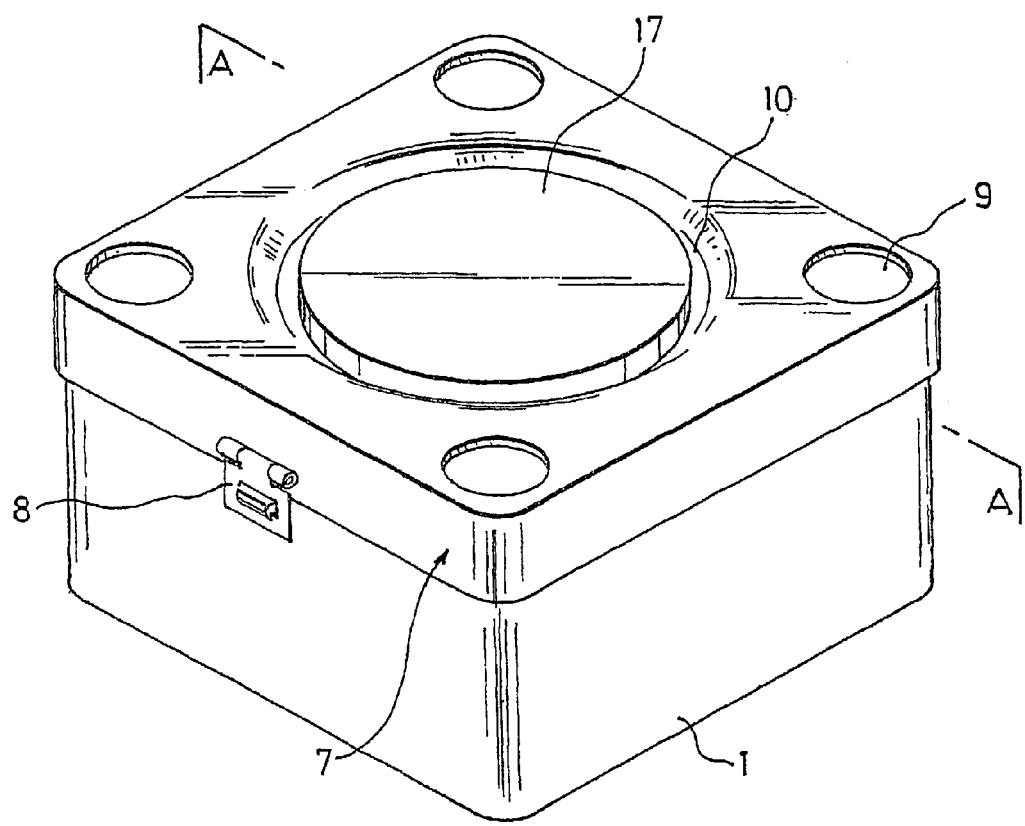
FIG. 1 is a perspective view of a first embodiment of a sterilisation set according to the invention.
Figure 2:
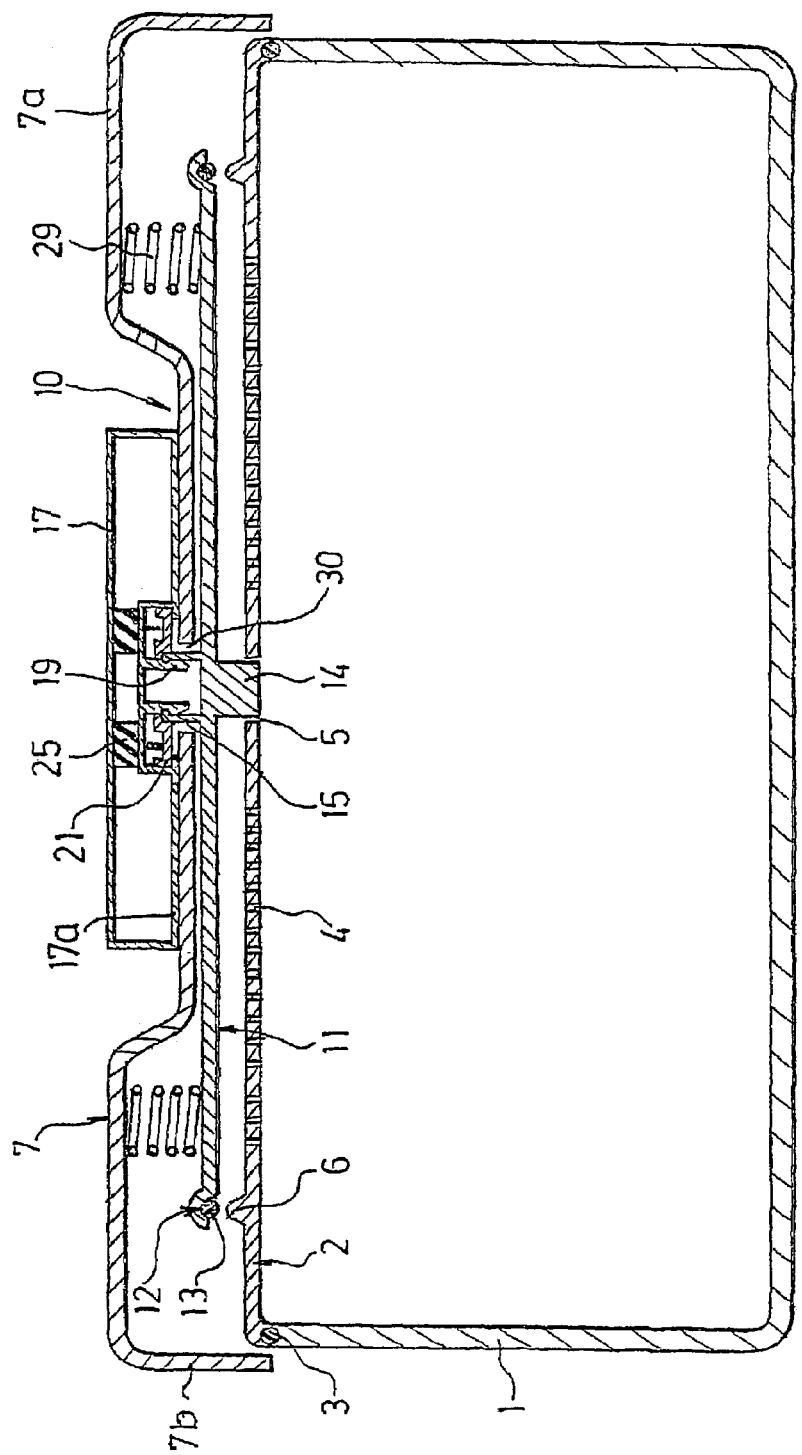
FIG. 2 is an axial section in a vertical plane A of this sterilisation set, in the open position of the valve.
Figure 3:
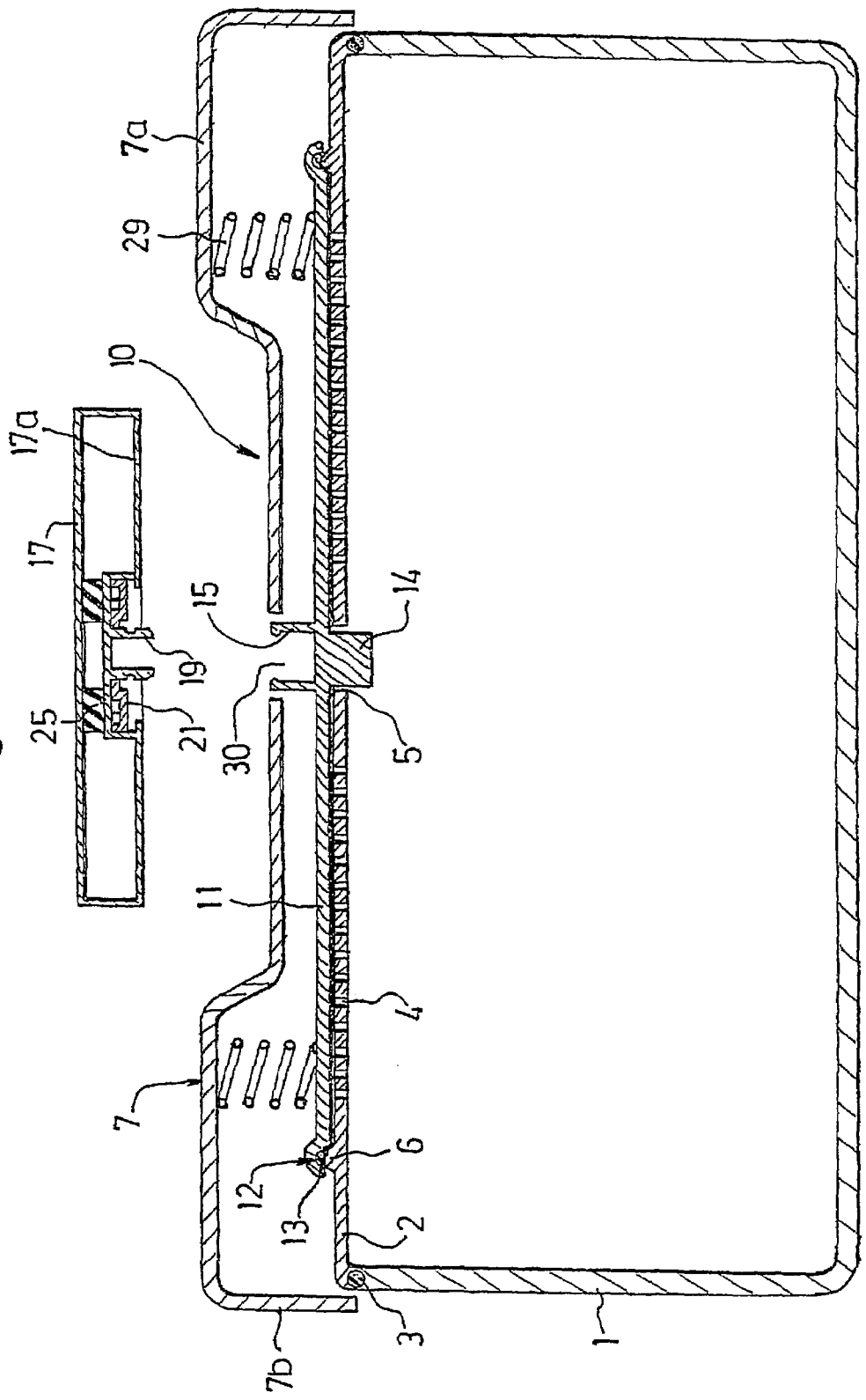
FIG. 3 is an axial section in the plane A, in the closed position of the valve.
Figure 4:
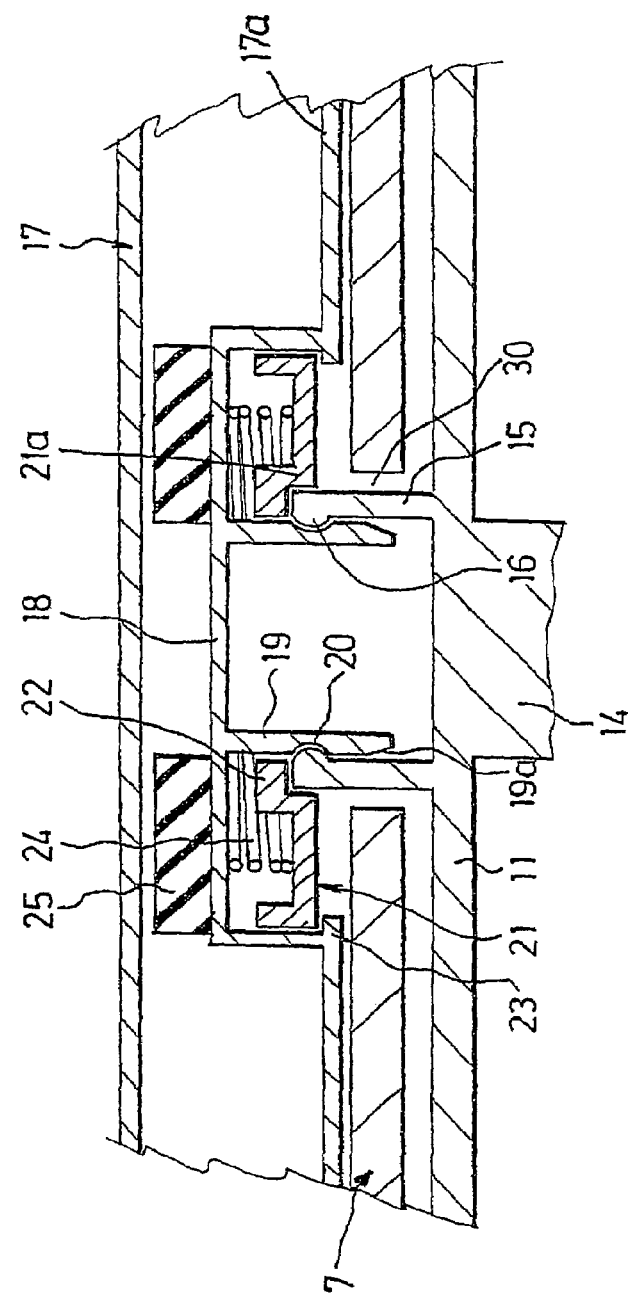
FIG. 4 is a detail partial section in the plane A, on an enlarged scale, of the catching and locking means.

The sterilisation set shown in FIGS. 1 to 4 firstly comprises a metallic receptacle 1 of conventional rectangular parallelepipedal shape on which rests a lid 2 with interposition, between said receptacle and lid, of a peripheral seal 3.

The lid 2 further has a circular central surface portion containing a plurality of small orifices such as 4 distributed over said surface portion. It also contains an axial orifice 5 of greater diameter.

The lid 2 lastly has, projecting relative to its upper face, a circular lip 6 formed on the circumference of the central surface portion containing orifices 4.

The sterilisation set further has an over-lid 7 having an upper wall 7a and a peripheral rim 7b on which are arranged conventional means 8 for locking said over-lid to the receptacle 1, in a position in which a volume is formed between the upper wall 7a of this over-lid 7 and the lid 2.

The upper wall 7a of this over-lid 7 contains orifices such as 9, of which there are four in the example formed in each of the corners of this upper wall and intended for the passage of a sterilising agent.

This wall 7a further possesses an indentation 10 in its central portion, defining a seat of generally cylindrical shape capable of accommodating the electronic apparatus described later on.

The sterilisation set additionally has a valve 11 consisting of a plate of dimensions matching the surface delimited by the lip 6 of the lid 2 and designed to cover this surface, said valve being equipped with a peripheral groove 12 accommodating a seal 13 arranged so as to cooperate with said lip 6, so as to ensure a sealed closure of the receptacle 1.

In order to guarantee a perfect coincidence between the lip 6 and the seal 13, the valve 11 further comprises, projecting relative to its lower face, an axial guiding pin 14 capable of moving in the axial orifice 5 of the lid 2.

This valve 11 lastly comprises axial catching means designed to:
- project into the indentation 10 of the over-lid 7 through an axial orifice 30 formed in the upper wall 7a of said over-lid, in an open position of the receptacle 1 in which said valve is separated from the lid 2,
- be situated set back from or at most flush with the upper wall 7a of the over-lid 7, in the closed position of the receptacle 1 in which the valve rests in a sealed manner on the lid 2.

These catching means consist of an axial ring 15, projecting relative to the upper face of the valve 11, consisting of flexible fingers capable of opening radially and equipped with an inner boss 16 towards their upper end.

In order to ensure that the valve 11 is pressed onto the lid 2, in the position of closing the receptacle 1, the sterilisation set further has springs such as 29 (or any equivalent elastic means such as laminae . . . ) arranged between said valve and the upper wall 7a of the over-lid 7, in regions situated outside the area of the orifices 9 and the indentation 10.

The sterilisation set according to the invention lastly comprises an independent electronic apparatus for recording the sterilisation parameters such as temperature and pressure, which is designed, furthermore, to lock the valve 11 in its position of opening the receptacle 1, during the sterilisation, and to release this valve 11 and permit its movement towards its position of closing the receptacle 1, under the action of the springs 29, once the sterilisation parameters are met.

This electronic apparatus 17 has a sealed housing made from a non-magnetic material, of a generally cylindrical shape and of dimensions designed to be accommodated in the indentation 10 of the over-lid 7.

This housing 17 integrates, in a conventional manner, the electronics and the power source (cells or batteries). It further has an axial indentation of cylindrical shape formed in the lower face 17a of said housing and intended to accommodate the means for locking the valve 11.

These locking means firstly comprise a rigid ring 19 extending axially from the bottom of the indentation 18, and of a length designed to project beyond the lower face of the housing 17. This ring 19, of a diameter designed to be inserted between the flexible fingers 15 of the valve 11, has an outer annular groove 20 formed so as to accommodate the bosses 16 of said flexible fingers, in the position of said valve in which it opens the receptacle 1.

This ring 19 further has a lower end section 19a possessing a conical outer face forming a ramp for insertion between the flexible fingers 15.

The locking means further have a locking member 21 made from a magnetic material and intended to lock the flexible fingers 15 in the position in which the boss 16 of the latter is lodged in the groove 20 of the ring 19.

To this end, this lock 21 is composed of an annular part arranged in the indentation 18 of the housing 17, in a peripheral annular volume of said indentation of a width corresponding to the distance between the peripheral wall of the latter and the outer face of the flexible fingers 15 when the boss 16 of the latter is lodged in the groove 20 of the ring 19.

The body of this annular part 21 possesses a U-shaped cross-section designed so that one of the limbs 21a of said U serves as a radial stop for locking the flexible fingers 15. This limb 21a is, furthermore, continued by an outer flange 22 perpendicular to said limb.

The locking means additionally comprise a spring 24 arranged in the indentation 18, between the bottom of the latter and the locking member 21 and designed to stress the latter towards its position of locking the flexible fingers. Lastly, a peripheral flange 23 coplanar with the lower wall 17a of the housing 17 projects into the inside of the indentation 18 so as to serve as a stop for the locking member 21 stressed by the spring 24.

Lastly, the electronic apparatus 17 comprises means for automatically disengaging the locking member 21 for producing the release of the flexible fingers 15, and consisting of an electromagnet 25 formed from a flat coil arranged in the housing 17a vertically in line with said locking member so as to be able to attract the latter, when commanded, counter to the action of the spring 24.

The alternative embodiment of the sterilisation set according to the invention shown in FIG. 5 is, as a whole, similar to that described above, and the same references have been used in this figure to denote the identical elements of the two embodiments.

The only difference lies in the fact that, according to this embodiment, the lid 2' and the over-lid 7' are made in one piece.

According to this embodiment, the over-lid 7' possesses a shape identical to that described above, whereas the lid 2' consists of an inner ring which is integral with the base of the peripheral rim 7b of said over-lid, on which the sealing lip 6 is formed and which delimits a central orifice 31 capable of being obturated by the valve 11.

The operation of the above-described sterilisation sets is as follows:

For setting, the electronic apparatus 17 is placed in its seat 10 on the over-lid 7. At this point, the valve 11 is normally closed. The springs 29 of the valve 11 are then compressed manually so that the fingers 15 enter the electronic apparatus 17, are forced onto the ring 19 through their flexibility and push the locking member 21 back by compressing the spring 24. When the boss 16 of the fingers 15 is opposite the groove 2 of the ring 19, and by virtue of the elasticity of said fingers, this boss 16 penetrates into this groove 10 thereby freeing a sufficient space for the locking member 21 to be pushed back towards its locking position by the spring 24. The system is then set, the valve 11 is kept open and the electronic apparatus 17 is locked to the over-lid 7 of the container. The over-lid 7 can now be put on the receptacle 1 of the container fitted with the lid 2, and locked to this receptacle 1.

During the sterilisation cycle, the electronic apparatus 17 measures and records the physical parameters (i.e. pressure and temperature). Its internal software compares the recorded data with programmed criteria. When these criteria have been fulfilled, the electronic apparatus 17 sends a power signal to the electromagnet 25 which is activated. The magnetic field which thereby results attracts the locking member 21 while compressing the spring 24, thus releasing the fingers 15. The force of the springs 29 tends to push the valve 11 away and to cause the boss 16 of the fingers 15 to escape from the groove 20. The valve 11 closes again and the electronic apparatus 17 is free.

The industrial application of this invention is the sterilisation of medico-surgical appliances or instruments in sealed containers with the assurance that the sterile state has been obtained (by parametric release) and will be preserved.

The invention claimed is:

1. Sterilisation set comprising:
    a container comprising a receptacle that is sealably closable,
    a valve inside the container facing an over-lid of said container, said over-lid being arranged to permit a sterilising agent to penetrate into said container,
    a seat supporting the valve and being inside the container so that said valve ensures the obturation of the receptacle in a closed position,
    a first sealing means for ensuring a seal between the valve and the seat in the closed position of said valve,
    elastic means for urging said valve towards its position of closing the receptacle,
    an apparatus that is arranged to be releasably carried on the over-lid of the container and that is linked to said valve with a catch, said apparatus holding said valve in an open position against the urging of said elastic means, said apparatus including electronic means for recording at least one sterilisation parameter during sterilisation,
    said apparatus having locking means for cooperating with said catch to keep said valve in its open position,
    said apparatus further comprising means for automatically disengaging the locking means for producing the release of the catch and allowing the movement of the valve towards its closed position under the action of the elastic means,
    said electronic means being programmed to activate the disengaging means when every sterilisation parameter is met, wherein: the over-lid is, of a shape designed to cap the receptacle and equipped with means for securing to said receptacle,
    the seat comprises a lid of a shape designed to cover the receptacle, and containing at least one orifice for the passage of a sterilising agent, which at least one orifice can be obturated by said valve in the closed position of the latter, and
    a second sealing means located between the receptacle and the seat for sealing the recepable in the closed position of the valve.

2. Sterilisation set as claimed in claim 1, wherein the lid and the over-lid are made in one piece so as to form an assembly separable from the receptacle and incorporating the valve.

3. Sterilisation set as claimed in claim 1, wherein the lid and the over-lid consist of two distinct elements, the valve being arranged under the over-lid and connected to the latter by the elastic means.

4. Sterilisation set as claimed in claim 1, wherein the lid contains a central orifice, the valve having a plate equipped at the lower face with a guiding pin that is arranged to slide into said orifice.

5. Sterilisation set as claimed in claim 1, wherein the lid has a central portion containing a plurality of orifices for the passage of a sterilising agent, the valve having a plate designed to cover said central portion, and said lid and valve having said first sealing means formed so as to be situated on the circumference of the lid central portion.

6. Sterilisation set as claimed in claim 1, wherein the over-lid has a central indented zone of dimensions designed to accommodate the electronic means.

7. Sterilisation set as claimed in claim 1, wherein the over-lid contains at least one orifice for the passage of a sterilising agent.

8. Sterilisation set comprising:
    a container comprising a receptacle that is sealably closable,
    a valve inside the container facing a sterilisation wall of said container, said wall being arranged to permit a sterilising agent to penetrate into said container,
    a seat supporting the valve and being inside the container so that said valve ensures the obturation of the receptacle in a closed position,
    sealing means for ensuring a seal between the valve and the seat in the closed position of said valve,
    elastic means for urging said valve towards its position of closing the receptacle,
    an apparatus that is arranged to be releasably carried on the sterilisation wall of the container and that is linked to said valve with a catch, said apparatus holding said valve in an open position against the urging of said elastic means, said apparatus including electronic means for recording at least one sterilisation parameter during sterilisation,
    said apparatus having locking means for cooperating with said catch to keep said valve in its open position,
    said apparatus further comprising means for automatically disengaging the locking means for producing the release of the catch and allowing the movement of the valve towards its closed position under the action of the elastic means,
    said electronic means being programmed to activate the disengaging means when every sterilisation parameter is met,
    wherein the catch and the elastic means are designed so that said catch does not project outside the sterilisation wall in the closed position of the valve.

9. Sterilisation set comprising:
    a container comprising a receptacle that is sealably closable, a valve inside the container facing a sterilisation wall of said container, said wall being arranged to permit a sterilising agent to penetrate into said container, a seat supporting the valve and being inside the container so that said valve ensures the obturation of the receptacle in a closed position, sealing means for ensuring a seal between the valve and the seat in the closed position of said valve, elastic means for urging said valve towards its position of closing the receptacle, an apparatus that is arranged to be releasably carried on the sterilization wall of the container and that is linked to said valve with a catch, said apparatus holding said valve in an open position against the urging of said elastic means, said apparatus including electronic means for recording at least one sterilisation parameter during sterilisation, said apparatus having locking means for cooperating with said catch to keep said valve in its open position, said apparatus further comprising means for automatically disengaging the locking means for producing the release of the catch and allowing the movement of the valve towards its closed position under the action of the elastic means, said electronic means being programmed to activate the disengaging means when every sterilisation parameter is met, wherein:

said catch and the locking means have two rings of shapes designed to fit into each other, and equipped with members for relative blocking in terms of axial translation, one of said rings being composed of radially flexible fingers, the locking means has a locking member arranged so as to be pushed back by the catch during the movement of the valve towards its open position, and stressed by further elastic means for keeping the locking member in a position of radially stopping the flexible fingers, and the automatic disengaging means are designed to bring about a movement of the locking member, countering the action of the further elastic means, towards a position in which it releases the flexible fingers.

10. Sterilisation set as claimed in claim 9, wherein:

the catch includes the ring composed of flexible fingers, said ring being of a shape designed to slide on the outside of the ring of the locking means, the locking means comprising an annular part of a shape designed to enclose the flexible fingers.

11. Sterilisation set as claimed in claim 10, wherein the ring of the locking means has an end section possessing a conical outer face forming a ramp for insertion inside the ring of the catch.

12. Sterilisation set as claimed in claim 9, wherein the blocking members of the rings comprise an annular boss and an annular groove of mating shapes, wherein one of the blocking members is formed on the flexible fingers at the end thereof.

13. Sterilisation set as claimed in claim 9, wherein the locking member is made from a magnetic material, the means for disengaging said locking member comprising an electromagnet.

14. Sterilisation set comprising:

a container comprising a receptacle that is sealably closable, a valve inside the container facing a sterilisation wall of said container, said wall being arranged to permit a sterilising agent to penetrate into said container, a seat supporting the valve and being inside the container so that said valve ensures the obturation of the receptacle in a closed position, sealing means for ensuring a seal between the valve and the seat in the closed position of said valve, elastic means for urging said valve towards its position of closing the receptacle, an apparatus that is arranged to be releasably carried on the sterilization wall of the container and that is linked to said valve with a catch, said apparatus holding said valve in an open position against the urging of said elastic means, said apparatus including electronic means for recording at least one sterilisation parameter during sterilisation, said apparatus having locking means for cooperating with said catch to keep said valve in its open position, said apparatus further comprising means for automatically disengaging the locking means for producing the release of the catch and allowing the movement of the valve towards its closed position under the action of the elastic means, said electronic means being programmed to activate the disengaging means when every sterilisation parameter is met, wherein said elastic means are arranged between the sterilisation wall and the valve so as to stress said valve towards its position of closing the receptacle.

\* \* \* \* \*